(12) United States Patent
Ross, Jr. et al.

(10) Patent No.: US 9,482,661 B2
(45) Date of Patent: Nov. 1, 2016

(54) SYNTHESIS AND USE OF ISOTOPICALLY LABELED MACROCYCLIC COMPOUNDS

(71) Applicant: DOW AGROSCIENCES LLC, Indianapolis, IN (US)

(72) Inventors: Ronald Ross, Jr., Zionsville, IN (US); Peter Lee Johnson, Indianapolis, IN (US); Kevin G. Meyer, Zionsville, IN (US)

( * ) Notice: Subject to any disclaimer, the term of this patent is extended or adjusted under 35 U.S.C. 154(b) by 174 days.

(21) Appl. No.: 14/139,040

(22) Filed: Dec. 23, 2013

(65) Prior Publication Data

US 2014/0186873 A1    Jul. 3, 2014

Related U.S. Application Data

(60) Provisional application No. 61/747,699, filed on Dec. 31, 2012.

(51) Int. Cl.

| | |
|---|---|
| *C12Q 1/02* | (2006.01) |
| *G01N 33/50* | (2006.01) |
| *C07D 213/79* | (2006.01) |
| *C07D 321/00* | (2006.01) |
| *C07D 405/12* | (2006.01) |
| *G01N 33/60* | (2006.01) |
| *A01N 43/40* | (2006.01) |
| *A01N 43/24* | (2006.01) |

(52) U.S. Cl.
CPC ........... *G01N 33/5097* (2013.01); *A01N 43/24* (2013.01); *A01N 43/40* (2013.01); *C07D 213/79* (2013.01); *C07D 321/00* (2013.01); *C07D 405/12* (2013.01); *G01N 33/60* (2013.01); *Y10T 436/142222* (2015.01); *Y10T 436/145555* (2015.01)

(58) Field of Classification Search
CPC .. G01N 35/5097; G01N 33/60; A01N 43/24; A01N 43/40; C07D 213/79; C07D 321/00; C07D 405/12; Y10T 436/42222; Y10T 436/14555
See application file for complete search history.

(56) References Cited

U.S. PATENT DOCUMENTS

| | | |
|---|---|---|
| 6,355,660 B1 | 3/2002 | Ricks et al. |
| 6,521,622 B1 | 2/2003 | Ricks et al. |
| 6,706,740 B2 | 3/2004 | Ricks et al. |
| 6,861,390 B2 | 3/2005 | Meyer et al. |
| 7,250,389 B1 | 7/2007 | Sakanaka et al. |
| 2004/0171838 A1 | 9/2004 | Meyer et al. |
| 2004/0186296 A1 | 9/2004 | Niyaz et al. |
| 2004/0192924 A1 | 9/2004 | Meyer et al. |
| 2007/0060579 A1 | 3/2007 | Wachendorff-Neumann et al. |
| 2007/0066629 A1 | 3/2007 | Blasco et al. |
| 2011/0082160 A1 | 4/2011 | Owen et al. |

FOREIGN PATENT DOCUMENTS

| | | |
|---|---|---|
| EP | 1 516 874 | 3/2005 |
| WO | WO 2009/040397 | 4/2009 |
| WO | WO 2012/070015 | 5/2012 |

OTHER PUBLICATIONS

Ukei et al. J. Antibiotics (1996) 49(7): 639-643.*
Klittich et al. Pest Management Science (2008) 64: 1267-1277.*
Anonymous, Synergistic Fungicidal Compositions of Heterocyclic Aromatic Amides and Triazoles, ip.com, Electronic Publication, 2004, 1-11.
Gisi, U., Synergistic Interaction of Fungicides in Mixtures, Symposium the American Phytopathological Society, 1996, 86(11), 1273-1279.
Science for a Better Life, Bayer Cropscience, Jun. 2008, p. 28.

* cited by examiner

*Primary Examiner* — Susan Hanley
(74) *Attorney, Agent, or Firm* — C. W. Amett; Faegre Baker Daniels LLP

(57) ABSTRACT

Disclosed herein are isotopically labeled antifungal antibiotics and related compounds. Also disclosed are methods for synthesizing these isotopically labeled molecules and using the same to study the distribution of these compounds in the biosphere as well as the products formed by the breakdown of these isotopically labeled compounds.

20 Claims, No Drawings

SYNTHESIS AND USE OF ISOTOPICALLY LABELED MACROCYCLIC COMPOUNDS

CROSS REFERENCE TO RELATED APPLICATIONS

This application claims the benefit of U.S. Provisional Patent Application Ser. No. 61/747,699 filed Dec. 31, 2012, which is expressly incorporated by reference herein.

FIELD OF THE INVENTION

Aspects of the invention include the preparation and use of isotopically labeled compounds including radiolabeled forms of the antifungal antibiotic UK-2A and related compounds.

BACKGROUND OF THE INVENTION

Isotopically labeled compounds are important tools in characterizing the role and fate of bioactive molecules in living systems and in ecosystems. Determining the mechanism of action and the fate of bioactive molecules may be instrumental in winning its approval for use as a crop protection chemical and in developing new generations of molecules that may have properties that are superior to those of the starting molecule. This process often times involves following the fate of a novel molecule or existing molecules being evaluated for new or expanded utility in the biosphere. For example, plants can be treated with appropriately labeled forms of the compounds under study. By tracking the fate of radiolabeled portions of the molecule it is possible to track the distribution of the compounds and moieties formed by the breakdown of these labeled compounds.

Such studies can be used to determine if particular molecules are phloem mobile, that is if they or possible dangerous compounds formed from the metabolism of these molecules can find their way into edible portions of the plants. Still other information that can be gleaned using this approach, including tracking the uptake of these molecules into various plants, fungi or insects in the biosphere.

Appropriately isotopically labeled versions of agriculturally active compounds can also be used to help identify the metabolites of these compounds. Of course, before these radiolabeled molecules can be used they must first be synthesized. The chemical or in some instances bio-synthesis of properly labeled bioactive molecules is sometimes extremely challenging. These syntheses include both the normal challenges of working with complex molecules and in some cases chemically toxic compounds, and the additional complication of using radioactive starting materials. These starting materials, in addition to generating radioactive products, by products, equipment, solvents, and the like, often require unique synthetic approaches to incorporate the isotope into the agriculturally active compound. Some of the materials and methods disclosed herein include methods of making and using such radiolabeled compounds.

SUMMARY OF THE INVENTION

Some aspects of the present invention are methods for the preparation and use of radiolabeled macrocyclic compounds including radiolabeled analogues and components of the antifungal antibiotic UK-2A.

Some aspects of the invention include radiolabeled compounds of the following formula:

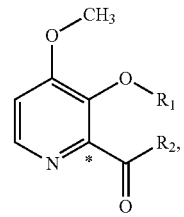

$* = {}^{14}C$ wherein $R_1$ is selected from the group consisting of H and

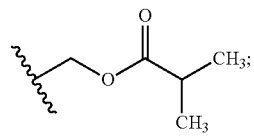

$R_2$ is selected from the group consisting of OH and

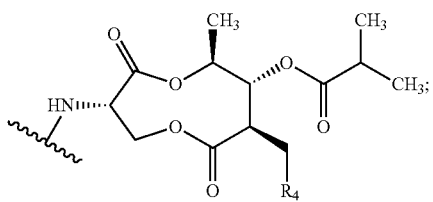

and $R_4$ is selected from the group consisting of phenyl (Ph), $({}^{13}C_6)$Ph, and (UL-${}^{14}$C)Ph, wherein UL is defined as uniformly labeled.

In some embodiments of the invention $R_1$ is

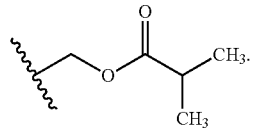

In still other embodiments $R_2$ is

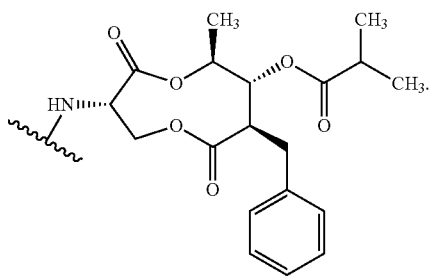 [SMILES: *N[C@H]1COC(=O)[C@H](Cc2ccccc2)[C@@H](OC(=O)C(C)C)[C@H](C)OC1=O]

And in some embodiments $R_1$ is H.

Some aspects of the invention include isotopically labeled compounds according to the following formula:

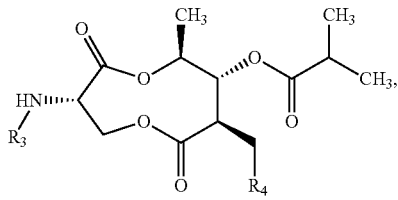

wherein $R_3$ is selected from the group consisting of

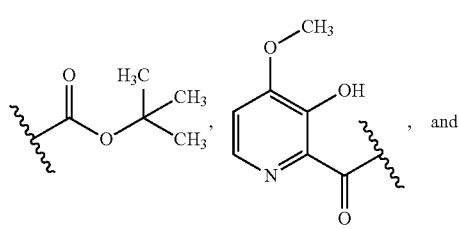, and

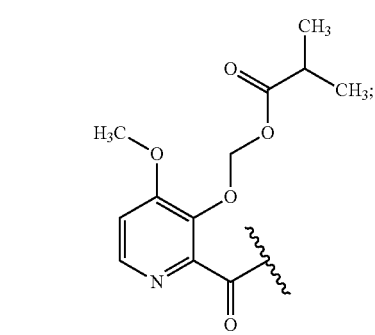

and $R_4$ is selected from the group consisting of ($^{13}C_6$)Ph and (UL-$^{14}$C)Ph.

In some embodiments of the invention $R_3$ is

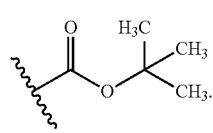

In still other embodiments $R_3$ is

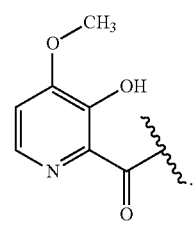 [SMILES: *C(=O)c1nccc(OC)c1O]

In yet other embodiments $R_3$ is

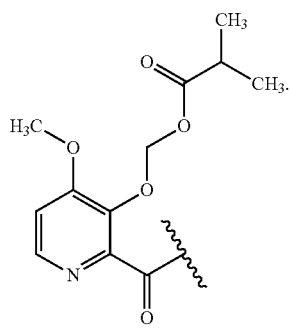 [SMILES: *C(=O)c1nccc(OC)c1OCOC(=O)C(C)C]

And in some embodiments $R_4$ is ($^{13}C_6$)Ph or (UL-$^{14}$C)Ph.

Some aspects of the invention include methods for studying the biosphere comprising the steps: analyzing samples of materials exposed to at least one isotopically labeled compound according to the instant disclosure and determining which samples include an isotopic signature from said compound. In some embodiments the sample is a portion of a plant. In some embodiments the sample is from a material that is a surface adjacent to a plant or connected to a surface adjacent to a plant. In some embodiments of the invention the isotopic signature is associated with a metabolite or degradation product of said compound.

In one exemplary embodiment, a radiolabeled compound is of the formula:

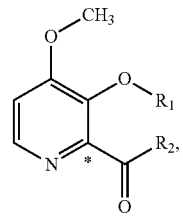

* = $^{14}$C wherein $R_1$ is selected from the group consisting of: H and

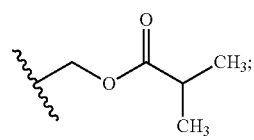 [SMILES: *COC(=O)C(C)C]

$R_2$ is selected from the group consisting of: OH and

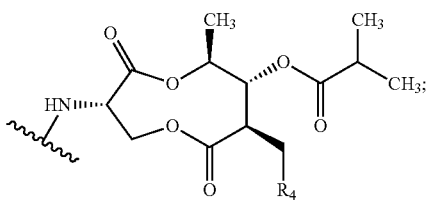

and $R_4$ is selected from the group consisting of Ph, Ph-$^{13}C_6$, and Ph-UL-$^{14}$C. In a more particular embodiment, $R_1$ is

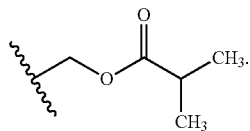

In another more particular embodiment, $R_1$ is H. In still another more particular embodiment, $R_2$ is:

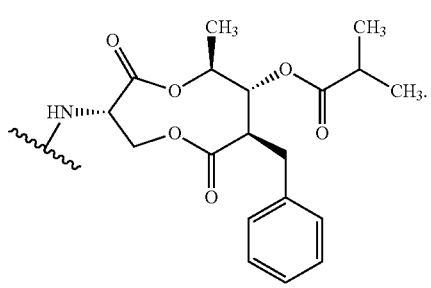 [SMILES: *N[C@H]1COC(=O)[C@H](Cc2ccccc2)[C@@H](OC(=O)C(C)C)[C@H](C)OC1=O]

In one exemplary embodiment, an isotopically labled compound is of the formula:

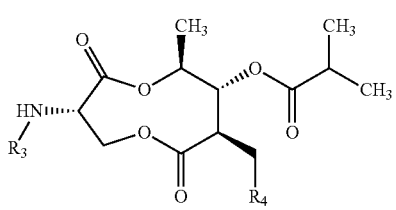

wherein $R_3$ is selected from the group consisting of: H,

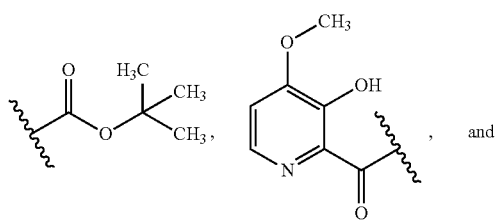

and $R_4$ is at least one atom selected from the group consisting of Ph-$^{13}C_6$, and Ph-UL-$^{14}C$. In a more particular embodiment, $R_3$ is

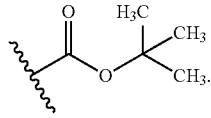 [SMILES: *C(=O)OC(C)(C)C]

In another more particular embodiment, $R_3$ is:

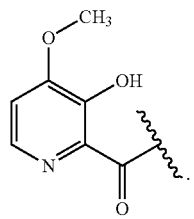 [SMILES: *C(=O)c1nccc(OC)c1O]

In still another more particular embodiment, $R_3$ is:

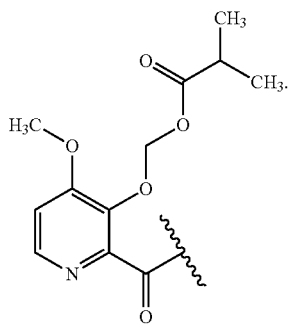 [SMILES: *C(=O)c1nccc(OC)c1OCOC(=O)C(C)C]

In still yet another more particular embodiment, $R_4$ is Ph-$^{13}C_6$. In another more particular embodiment, $R_4$ is Ph-UL-$^{14}C$.

In one exemplary embodiment, a method for studying the biosphere is provided. The method includes analyzing one or more samples exposed to an isotopically labeled compound of the formula:

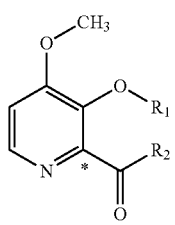

$* = {}^{14}C$ wherein $R_1$ is selected from the group consisting of H and

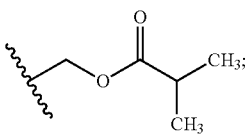

$R_2$ is selected from the group consisting of OH and

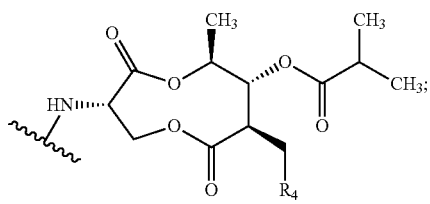

and $R_4$ is selected from the group consisting of Ph, Ph-$^{13}C_6$, and Ph-UL-$^{14}C$. The method further includes determining which samples, if any, include an isotopically labeled signature from said compound. In a more particular embodiment, the sample is a portion of a plant. In another more particular embodiment, the sample is from a surface adjacent to a plant. In still another more particular embodiment, the sample is from a material that is in communication with a surface adjacent to a plant. In yet still another more particular embodiment, the isotopically labeled signature is contained in a portion of said compound.

In one exemplary embodiment, another method for studying the biosphere is provided. The method includes analyzing one or more samples exposed to an isotopically labeled compound of the following formula:

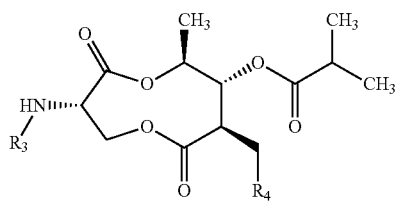

wherein $R_3$ is selected from the group consisting of:

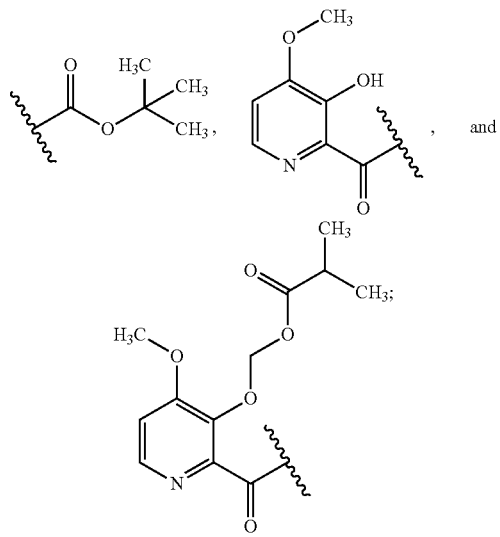

and $R_4$ is at least one atom selected from the group consisting of Ph-$^{13}C_6$, and Ph-UL-$^{14}C$. The method further includes determining which samples, if any, include an isotopically labeled signature from said compound. In a more particular embodiment, the sample is a portion of a plant. In another more particular embodiment, the sample is from a surface adjacent to a plant. In still another more particular embodiment, the sample is from a material that is in communication with a surface adjacent to a plant. In yet still another more particular embodiment, the isotopically labeled signature is contained in a portion of said compound.

In one exemplary embodiment, a process for the preparation of radiolabeled compounds of the Formula:

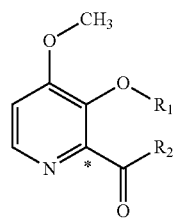

$* = {}^{14}C$ is provided, wherein $R_1$ is selected from the group consisting of H and

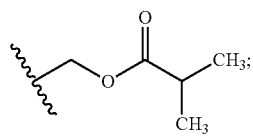 [SMILES: *COC(=O)C(C)C]

and $R_2$ is

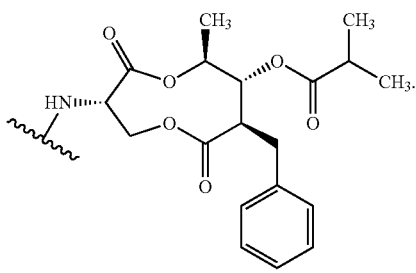 [SMILES: *N[C@H]1COC(=O)[C@H](Cc2ccccc2)[C@@H](OC(=O)C(C)C)[C@H](C)OC1=O]

The process includes (a) contacting a solution of a compound of Formula A in an aprotic solvent with a compound of Formula B, where Formula A is:

A

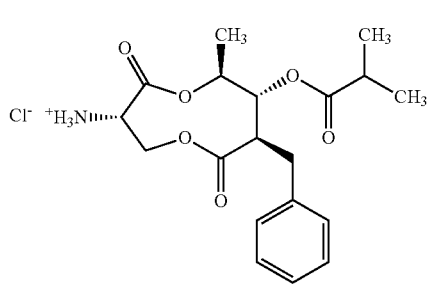

and Formula B is:

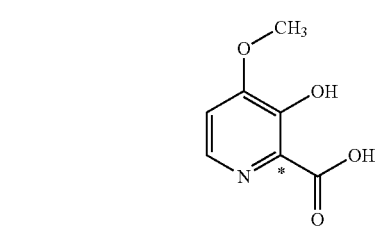

* = $^{14}C$ followed by the sequential treatment with an organic amine base and a peptide coupling reagent to produce a compound of Formula C:

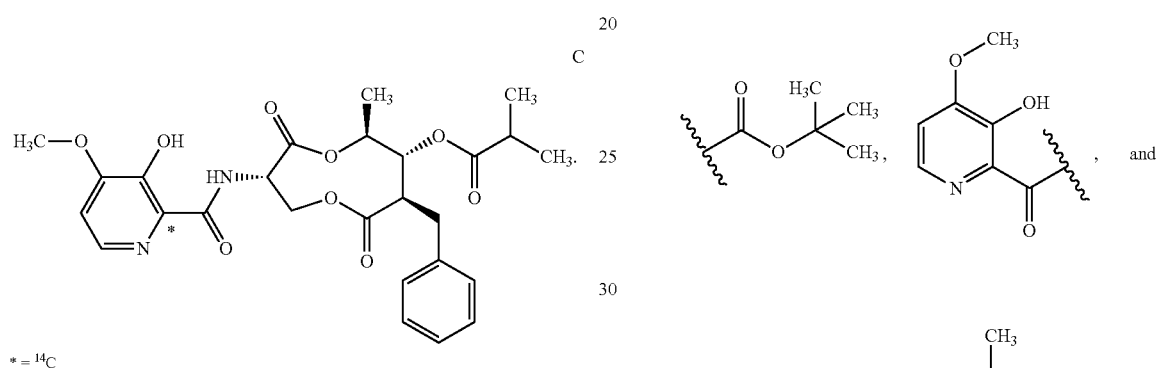

* = $^{14}C$

The process further includes (b) contacting a solution of the picolinamide of Formula C in a polar solvent with an alkali carbonate base, followed by treatment with iodomethyl isobutyrate to produce a compound of Formula D:

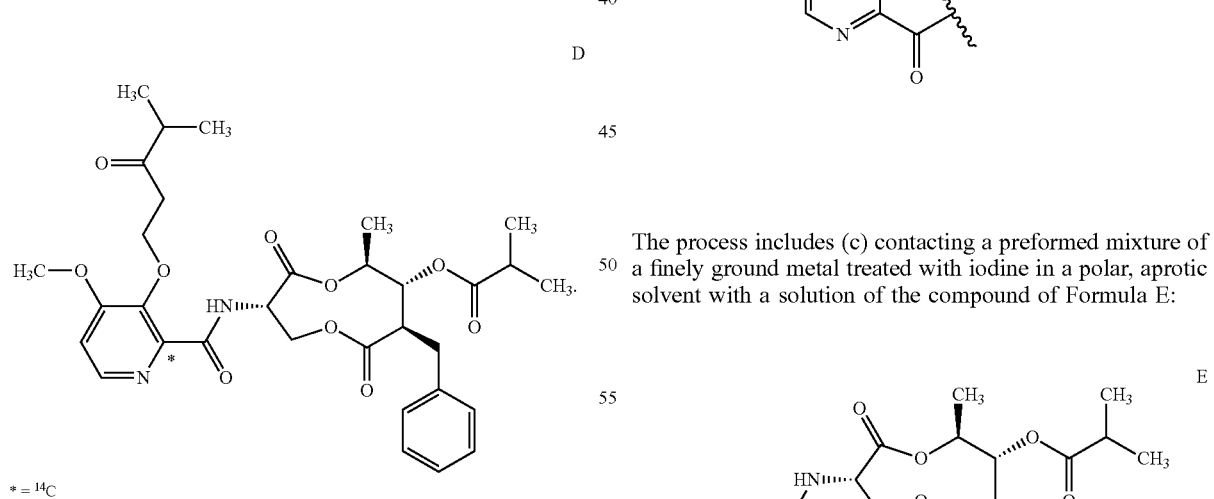

* = $^{14}C$

In a more particular embodiment, the aprotic solvent is $CH_2Cl_2$, the organic amine base is a mixture of 4-methylmorpholine and DMAP, and the peptide coupling reagent is HATU in step (a). In another more particular embodiment, the polar solvent is acetone and the alkali carbonate base is $Na_2CO_3$ in step (b).

In one exemplary embodiment, a process for the preparation of isotopically labeled compounds of the formula:

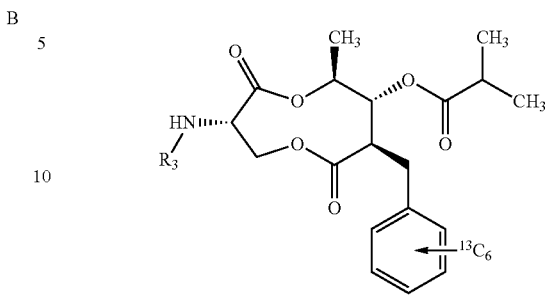

is provided, wherein $R_3$ is selected from the group consisting of: H,

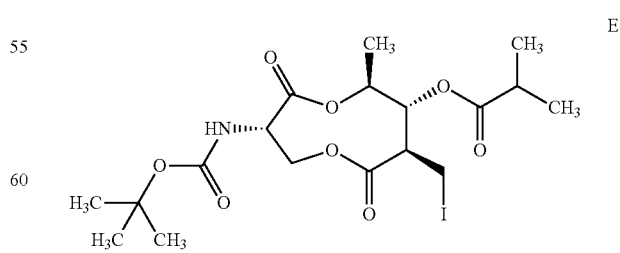

The process includes (c) contacting a preformed mixture of a finely ground metal treated with iodine in a polar, aprotic solvent with a solution of the compound of Formula E:

E in a polar, aprotic solvent, followed by treatment with ($^{13}C_6$)-iodobenzene and a palladium catalyst at an elevated temperature to produce a compound of Formula F:

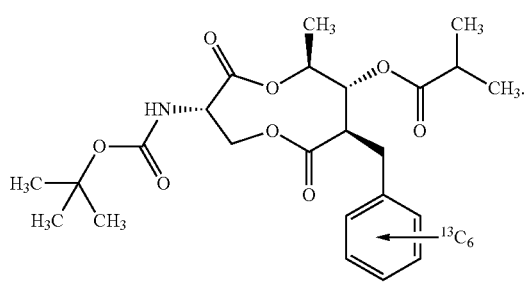

F

The process further includes (d) contacting a solution of the Boc-protected aminolactone of Formula F in a polar, aprotic solvent with a solution of a mineral acid in a polar, aprotic solvent to produce a compound of Formula G:

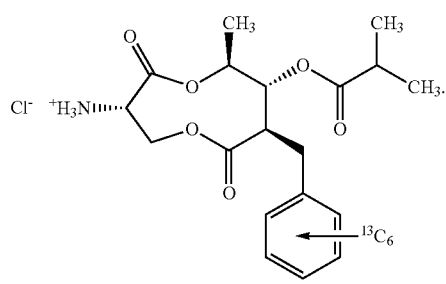

G

The process further includes (e) contacting a solution of the amine hydrochloride of Formula G in an aprotic solvent with an inorganic, alkali carbonate base or an organic amine base to produce a compound of Formula H

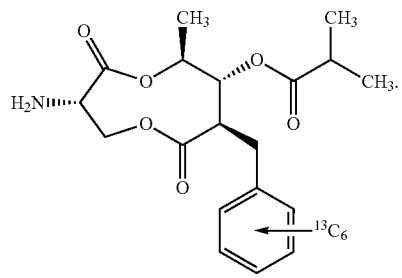

H

The process further includes (f) contacting a solution of the amino macrocycle of Formula H in an aprotic solvent, generated as described in step (e) or in situ, with a compound of Formula I:

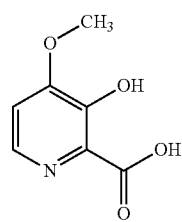

I followed by treatment with an organic amine base and a peptide coupling reagent to produce a compound of Formula J:

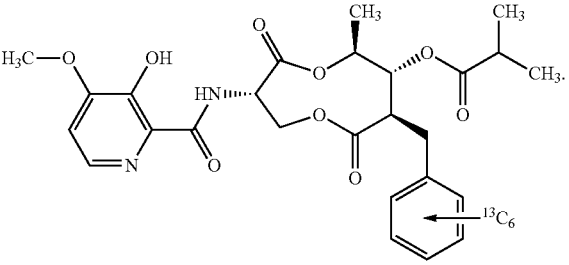

J

The process further includes contacting a solution of the picolinamide of Formula J in a polar solvent with an alkali carbonate base followed by iodomethyl isobutyrate to produce a compound of Formula K:

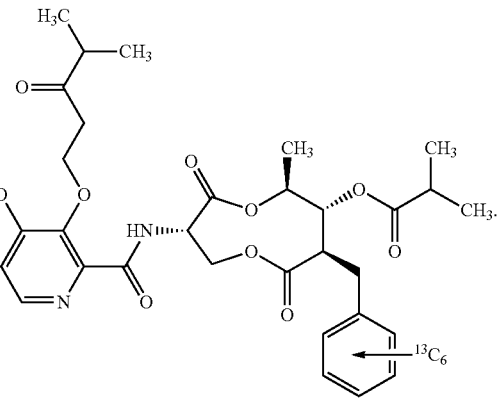

K

In a more particular embodiment, in step (c) the finely ground metal is zinc dust, the polar aprotic solvent is DMF, the palladium catalyst is $(PdCl_2[P(o\text{-}Tol)_3]_2)$, and the temperature is about (i) 40-50° C. for 30 minutes followed by about (ii) 50-60° C. for 60 minutes. In another more particular embodiment, in step (d), the mineral acid is hydrogen chloride and the polar, aprotic solvent is dioxane. In another more particular embodiment, in step (e), the aprotic solvent is $CH_2Cl_2$, the alkali carbonate base is NaHCO3 and the organic amine base is 4-methylmorpholine. In another more particular embodiment, in step (f), the organic amine base is a mixture of 4-methylmorpholine and catalytic DMAP, the peptide coupling reagent is HATU, and the aprotic solvent is $CH_2Cl_2$. In another more particular embodiment, in step (g), the alkali carbonate base is $K_2CO_3$ and the polar solvent is acetone.

In one exemplary embodiment, a process of the preparation of radiolabeled compounds of the Formula:

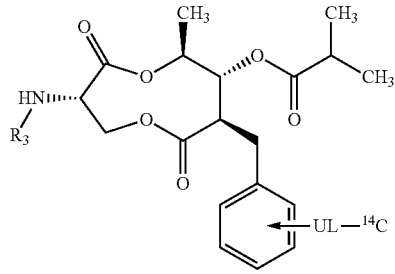

is provided, wherein $R_3$ is selected from the group consisting of: H,

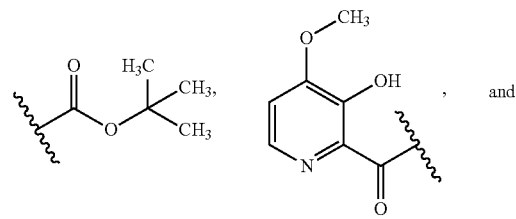

and

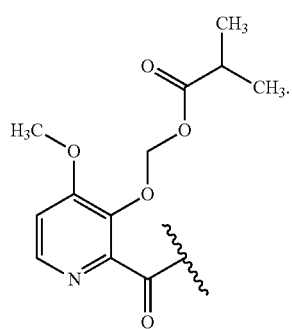

The process includes (h) contacting a preformed mixture of a finely ground metal treated with iodine in a polar, aprotic solvent with a solution of the compound of Formula E:

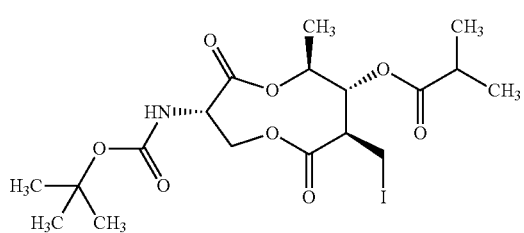

in a polar, aprotic solvent, followed by treatment with (UL-$^{14}$C)-iodobenzene and a palladium catalyst at an elevated temperature to produce a compound of Formula L:

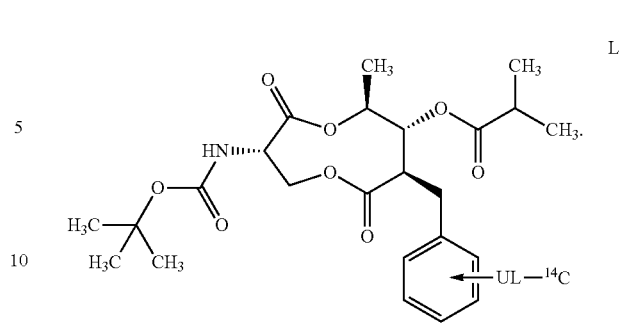

The process further includes (i) contacting a solution of the Boc-protected aminolactone of Formula L in a polar, aprotic solvent with a solution of a mineral acid in a polar, aprotic solvent to produce a compound of Formula M:

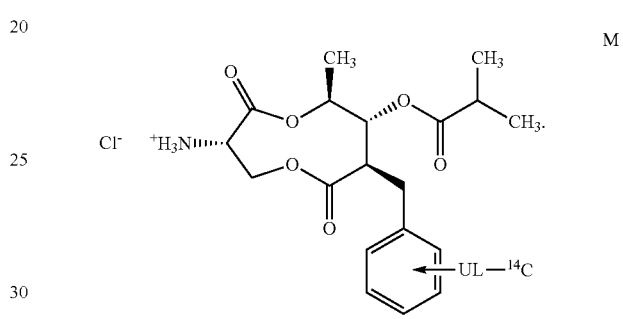

The process further includes (j) contacting a solution of the amine hydrochloride of Formula M in an aprotic solvent with an inorganic, alkali carbonate base or an organic amine base to produce a compound of Formula N:

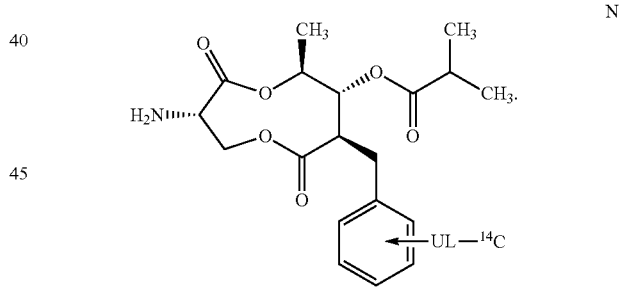

The process further includes (k) contacting a solution of the amino macrocycle of Formula N in an aprotic solvent, generated as described in step (e) or in situ, with a compound of Formula I:

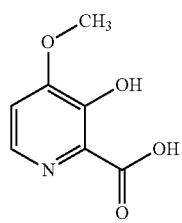

followed by a peptide coupling reagent and an organic amine base to produce a compound of Formula O:

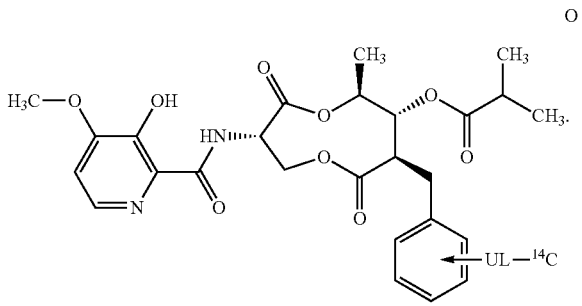

The process further includes (1) contacting a solution of the picolinamide of Formula O in a polar solvent with an alkali carbonate base followed by iodomethyl isobutyrate to produce a compound of Formula P:

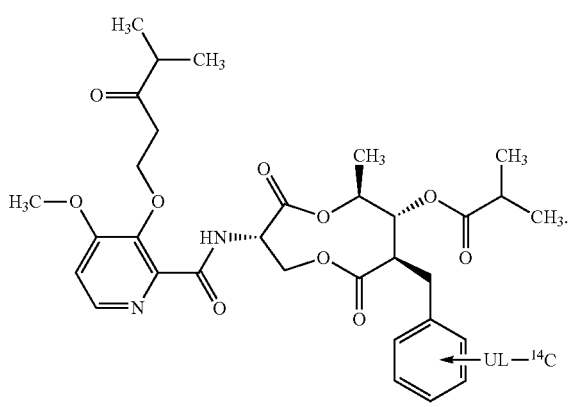

In a more particular embodiment, in step (h) the finely ground metal is zinc dust, the polar aprotic solvent is DMF, the palladium catalyst is (PdCl$_2$[P(o-Tol)$_3$]$_2$), and the temperature is about (i) 40-50° C. for 30 minutes followed by about (ii) 50-60° C. for 120 minutes. In another more particular embodiment, in step (i), the mineral acid is hydrogen chloride and the polar, aprotic solvent is dioxane. In another more particular embodiment, in step (j), the aprotic solvent is CH$_2$Cl$_2$, the alkali carbonate base is NaHCO$_3$ and the organic amine base is 4-methylmorpholine. In another more particular embodiment, in step (k), the organic amine base is a mixture of 4-methylmorpholine and catalytic DMAP, the peptide coupling reagent is HATU, and the aprotic solvent is CH$_2$Cl$_2$. In another more particular embodiment, in step (l), the alkali carbonate base is K$_2$CO$_3$ and the polar solvent is acetone.

DETAILED DESCRIPTION OF THE INVENTION

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of this disclosure and the claims.

As used herein, unless explicitly stated otherwise or clearly implied otherwise the term 'about' refers to a range of values plus or minus 10 percent, e.g. about 1.0 encompasses values from 0.9 to 1.1.

The present invention concerns the preparation of radiolabeled 3-hydroxy-4-methoxypicolinic acid. (2-$^{14}$C)pyridin-3-ol (Compound 2) was prepared by the method described in *J Labelled Comp Rad* 1992, 31, 615. The radiolabeled pyridin-3-ol was then converted to the novel 3-hydroxy-4-methoxy(2-$^{14}$C)pyridine-2-carboxylic acid (Compound 6) using the method described in *Tetrahedron Lett.* 1998, 39, 4363 and substantially modified by using radiolabeled starting material.

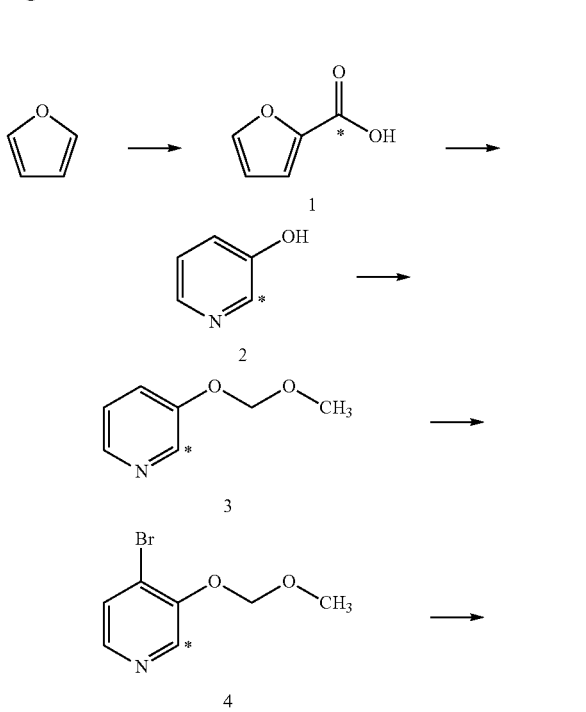

* = $^{14}$C

Some embodiments include the synthesis of (3S,6S,7R,8R)-8-benzyl-3-({[3-hydroxy-4-methoxy(2-$^{14}$C)pyridin-2-yl]carbonyl}amino)-6-methyl-4,9-dioxo-1,5-dioxonan-7-yl-2-methylpropanoate (Compound 8) by contacting 3-hydroxy-4-methoxy(2-$^{14}$C)pyridine-2-carboxylic acid (Compound 6) with (3S,6S,7R,8R)-8-benzyl-3-[(tert-butoxycarbonyl)amino]-6-methyl-4,9-dioxo-1,5-dioxonan-7-yl 2-methylpropanoate (Compound 7).

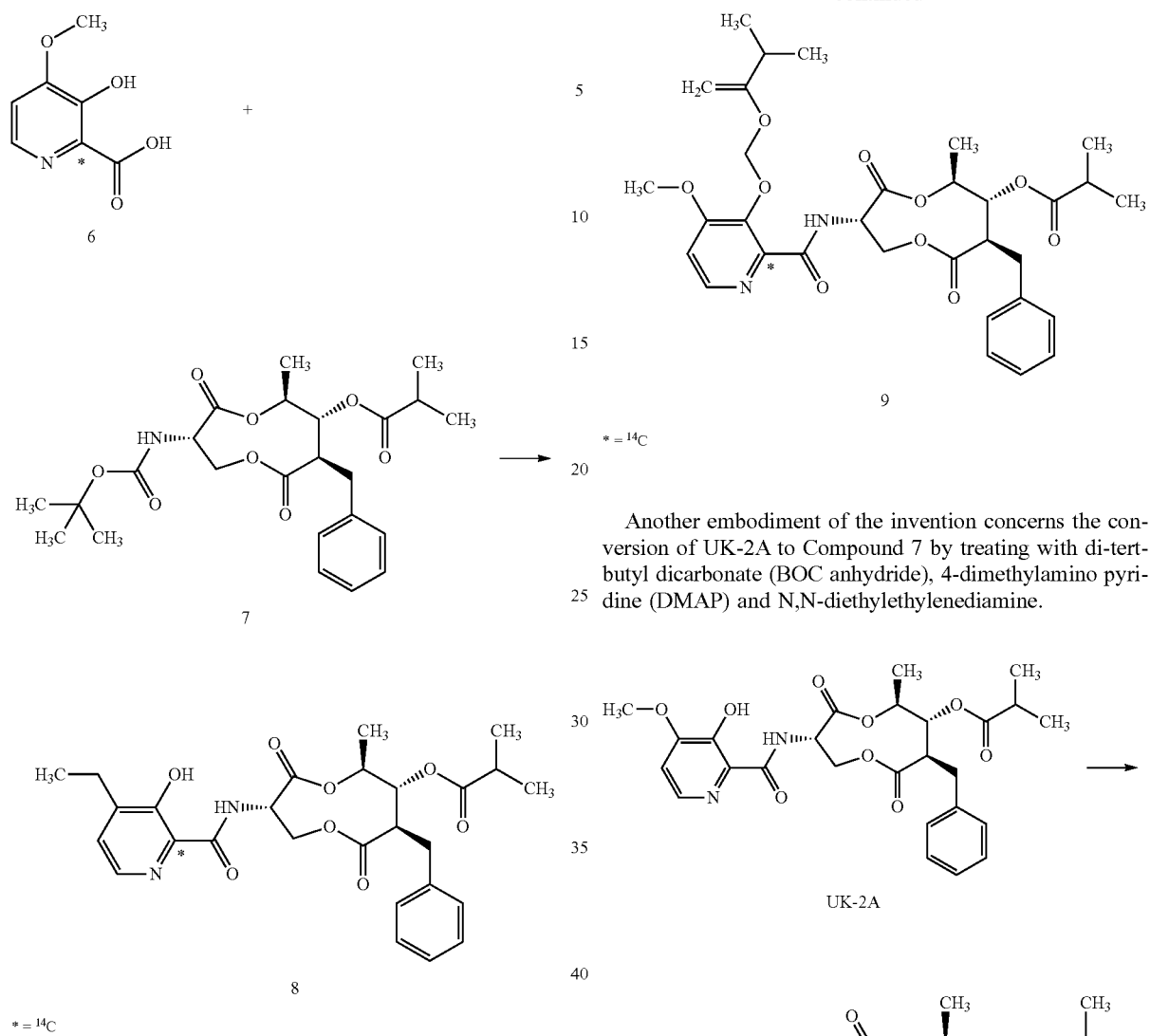

Another embodiment of the invention concerns the conversion of UK-2A to Compound 7 by treating with di-tert-butyl dicarbonate (BOC anhydride), 4-dimethylamino pyridine (DMAP) and N,N-diethylethylenediamine.

The present invention concerns the preparation of (3S, 6S,7R,8R)-8-benzyl-3-({[4-methoxy-3-{[(2-methylpropanoyl)oxy]methoxy}(2-$^{14}$C)pyridin-2-yl]carbonyl}amino)-6-methyl-4,9-dioxo-1,5-dioxonan-7-yl 2-methylpropanoate (Compound 9) by contacting (3S,6S,7R,8R)-8-benzyl-3-({[3-hydroxy-4-methoxy(2-$^{14}$C)pyridin-2-yl]carbonyl}amino)-6-methyl-4,9-dioxo-1,5-dioxonan-7-yl-2-methylpropanoate (Compound 8) with iodomethyl isobutyrate.

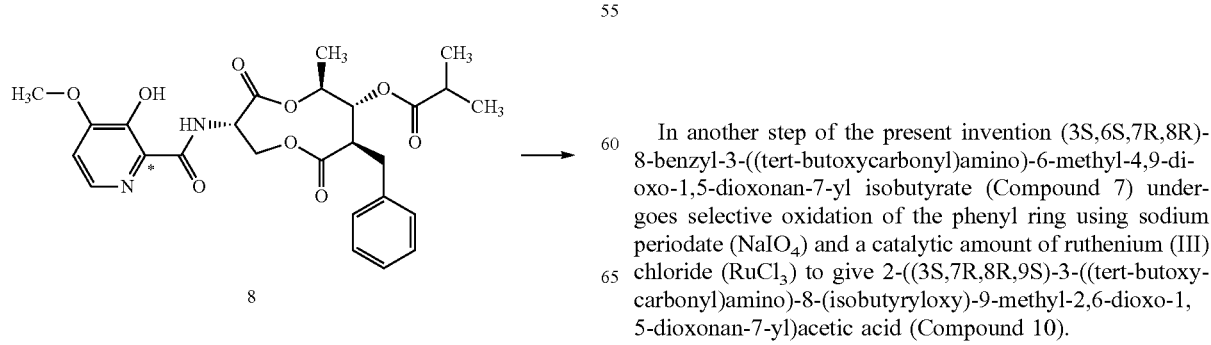

In another step of the present invention (3S,6S,7R,8R)-8-benzyl-3-((tert-butoxycarbonyl)amino)-6-methyl-4,9-dioxo-1,5-dioxonan-7-yl isobutyrate (Compound 7) undergoes selective oxidation of the phenyl ring using sodium periodate (NaIO$_4$) and a catalytic amount of ruthenium (III) chloride (RuCl$_3$) to give 2-((3S,7R,8R,9S)-3-((tert-butoxycarbonyl)amino)-8-(isobutyryloxy)-9-methyl-2,6-dioxo-1,5-dioxonan-7-yl)acetic acid (Compound 10).

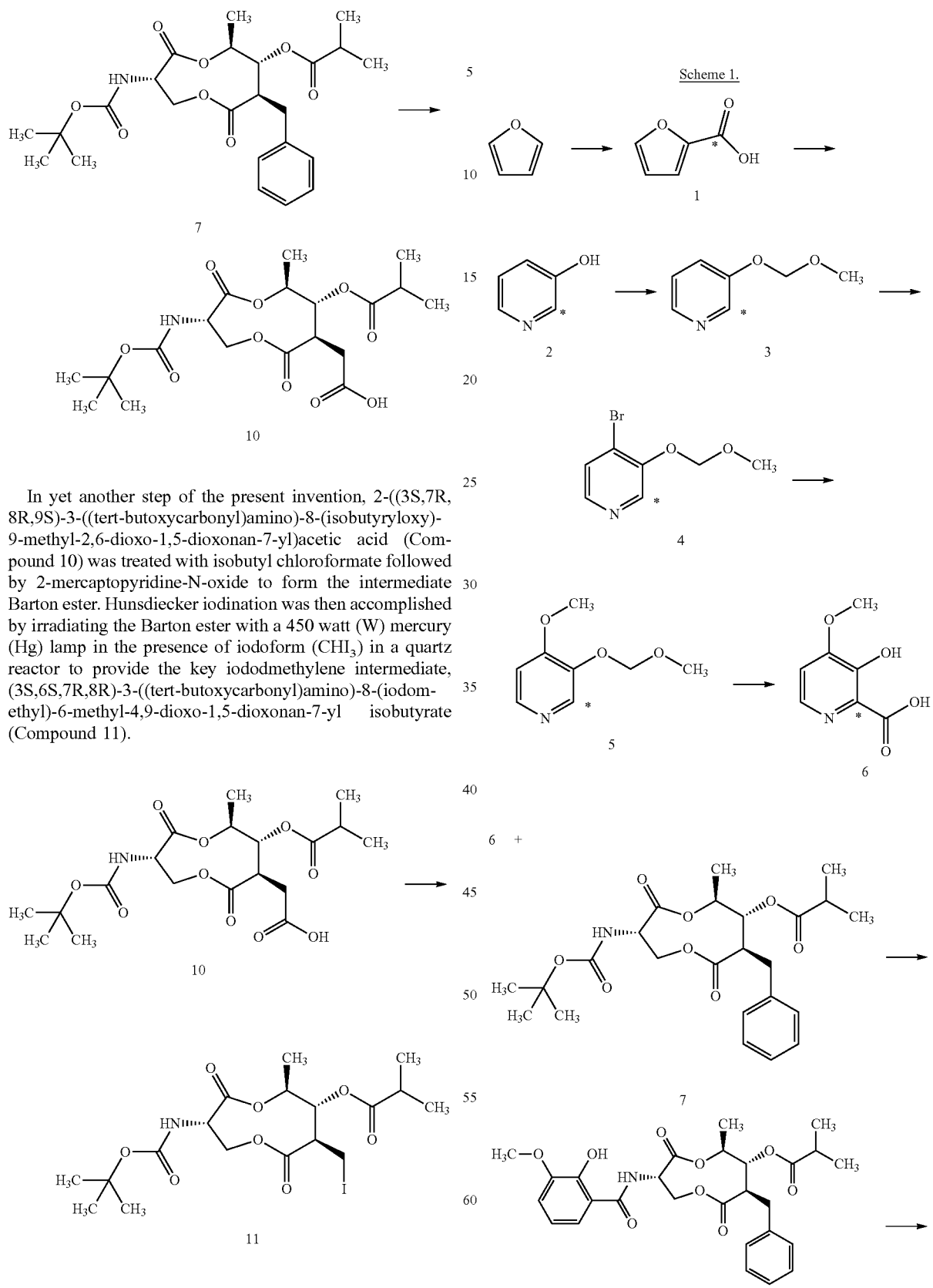

SCHEMES AND EXAMPLES

Scheme 1.

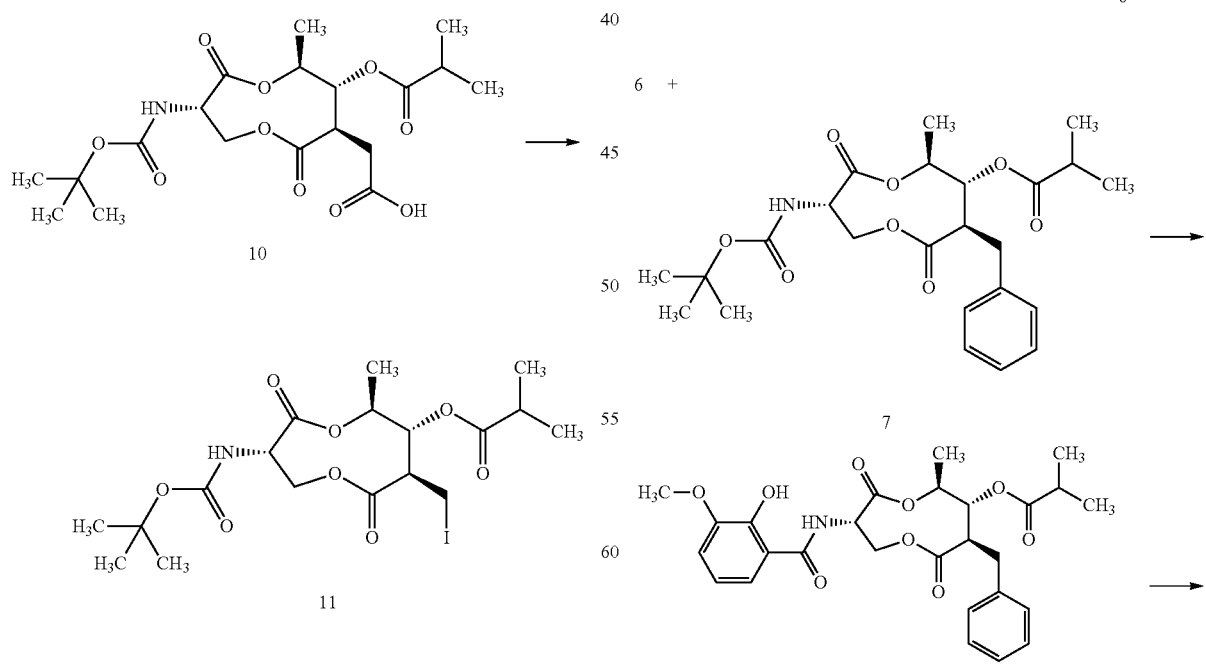

In yet another step of the present invention, 2-((3S,7R,8R,9S)-3-((tert-butoxycarbonyl)amino)-8-(isobutyryloxy)-9-methyl-2,6-dioxo-1,5-dioxonan-7-yl)acetic acid (Compound 10) was treated with isobutyl chloroformate followed by 2-mercaptopyridine-N-oxide to form the intermediate Barton ester. Hunsdiecker iodination was then accomplished by irradiating the Barton ester with a 450 watt (W) mercury (Hg) lamp in the presence of iodoform ($CHI_3$) in a quartz reactor to provide the key iododmethylene intermediate, (3S,6S,7R,8R)-3-((tert-butoxycarbonyl)amino)-8-(iodomethyl)-6-methyl-4,9-dioxo-1,5-dioxonan-7-yl isobutyrate (Compound 11).

The following examples are presented to illustrate the invention, these examples are presented by way of illustration and not limitation.

-continued

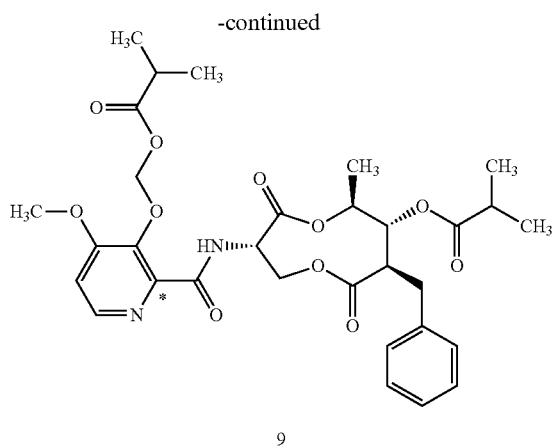

9

* = $^{14}C$

Example 1, Steps 1 Through 6

Preparation of 3-hydroxy-4-methoxy(2-$^{14}$C)pyridine-2-carboxylic acid (Compound 6)

(2-$^{14}$C)pyridin-3-ol (Compound 2) was prepared by the method described in *J Labelled Comp Rad* 1992, 31, 615. The radiolabeled pyridin-3-ol was then converted to 3-hydroxy-4-methoxy(2-$^{14}$C)pyridine-2-carboxylic acid (Compound 6) using the method described in *Tetrahedron Lett.* 1998, 39, 4363.

Example 1, Steps 7a

Preparation of (3S,6S,7R,8R)-8-benzyl-3-[(tert-butoxycarbonyl)amino]-6-methyl-4,9-dioxo-1,5-dioxonan-7-yl 2-methylpropanoate (Compound 7)

To a dry 2000 milliliter (mL) round bottom flask equipped with mechanical stirrer, nitrogen ($N_2$) inlet, addition funnel, and thermometer, was charged (3S,6S,7R,8R)-8-benzyl-3-{[(3-hydroxy-4-methoxypyridin-2-yl)carbonyl]amino}-6-methyl-4,9-dioxo-1,5-dioxonan-7-yl2-methylpropanoate (100 grams (g), 194 millimole (mmol)), DMAP (2.4 g, 19.4 mmol), and anhydrous acetonitrile ($CH_3CN$; 1000 mL). To this stirred suspension was added di-tert-butyl dicarbonate ($BOC_2O$; 93 g, 428 mmol) in portions. This mixture was stirred at ambient temperature for 1 hour (h), after which N,N-diethylethylenediamine (24.8 g, 214 mmol) was added dropwise over 20 minutes (min). The reaction was stirred at room temperature for 2 days (d). The $CH_3CN$ was removed on a rotary evaporator, and the residue was dissolved in diethyl ether ($Et_2O$; 1500 mL). This solution was washed with saturated aqueous (aq) sodium bicarbonate solution ($NaHCO_3$; 500 mL), 0.1Normal (N) aq hydrogen chloride HCl (500 mL), water (500 mL) and saturated aq sodium chloride (NaCl) solution (brine; 500 mL). The ether solution was dried over anhydrous magnesium sulfate ($MgSO_4$), filtered through a plug of silica gel, and concentrated under vacuum on a rotary evaporator. The resulting crude white solid (22 g) was dissolved in dichloromethane ($CH_2Cl_2$; 50 mL) and purified by silica gel flash chromatography ($SiO_2$, 0→100% ethyl acetate (EtOAc)/hexanes) to yield the title compound as a crystalline white solid (18 g, 20%): $^1$H NMR (400 MHz, $CDCl_3$) δ 7.29-7.16 (m, 4H), 7.15-7.08 (m, 2H), 5.17 (t, J=9.7 Hz, 3H), 4.91 (dq, J=12.5, 6.3 Hz, 1H), 4.80 (s, 1H), 3.44 (s, 1H), 3.02-2.84 (m, 2H), 2.62 (ddd, J=20.9, 18.0, 9.6 Hz, 2H), 1.60 (s, 2H), 1.43 (s, 9H), 1.30 (d, J=6.3 Hz, 3H), 1.23 (dd, J=7.0, 2.2 Hz, 6H); $^{13}$C NMR (101 MHz, $CDCl_3$) δ 175.62, 171.72, 137.93, 128.73, 128.57, 126.66, 77.33, 77.02, 76.70, 75.05, 74.45, 51.94, 34.53, 34.11, 28.23, 18.98, 18.96, 17.85; ESIMS m/z 462.5 ([M–H]$^-$).

Example 1, Step 7b

Preparation of (3S,6S,7R,8R)-8-benzyl-3-({[3-hydroxy-4-methoxy(2-$^{14}$C)pyridin-2-yl]carbonyl}amino)-6-methyl-4,9-dioxo-1,5-dioxonan-7-yl 2-methylpropanoate (Compound 8)

To a dry 50 mL round bottom flask equipped with magnetic stirrer, was charged (3S,6S,7R,8R)-8-benzyl-3-[(tert-butoxycarbonyl)amino]-6-methyl-4,9-dioxo-1,5-dioxonan-7-yl 2-methylpropanoate (570 milligrams (mg), 1.23 mmol) and 3.0 mL of 4 Molar (M) HCl in dioxane. After 10 min, an additional 3.0 mL of dioxane was added to facilitate stirring. The flask was sealed with a rubber septum and stirred at room temperature for an additional 4 h. The resulting thick, gelatinous mixture was concentrated by rotary evaporation and the crude product was triturated in $CH_2Cl_2$ (10 mL) and again concentrated in vacuo on a rotary evaporator. The residual white solid was suspended in $CH_2Cl_2$ (10 mL) and 3-hydroxy-4-methoxy(2-$^{14}$C)pyridine-2-carboxylic acid (274 mg, 1.59 mmol) was added in one portion. To this mixture was sequentially added 4-methylmorpholine (746 mg, 7.38 mmol), 2-(7-aza-1H-benzotriazole-1-yl)-1,1,3,3-tetramethyluronium hexafluorophosphate (HATU; 701 mg, 1.84 mmol), and DMAP (15 mg, 0.123 mmol), and the heterogeneous mixture was stirred at room temperature under a $N_2$ atmosphere for 16 h. The resulting clear, pale-yellow solution was concentrated under a stream of $N_2$, and the residue was dissolved in $CH_2Cl_2$ (5 mL) and purified by flash chromatography ($SiO_2$, 100% EtOAc) to yield the title compound as a crystalline white solid (539 mg, 85%): structure conforms by HPLC (retention time match to authentic unlabeled standard) and diode-array UV spectrum.

Example 1, Step 8

Preparation of (3S,6S,7R,8R)-8-benzyl-3-({[4-methoxy-3-{[(2-methylpropanoyl)oxy]methoxy}(2-$^{14}$C)pyridin-2-yl]carbonyl}amino)-6-methyl-4,9-dioxo-1,5-dioxonan-7-yl2-methylpropanoate (Compound 9)

To a dry 50 mL round bottom flask equipped with magnetic stirrer and $N_2$ inlet was charged (3S,6S,7R,8R)-8-benzyl-3-({[3-hydroxy-4-methoxy(2-$^{14}$C)pyridin-2-yl]carbonyl}amino)-6-methyl-4,9-dioxo-1,5-dioxonan-7-yl 2-methylpropanoate (479.5 mg, 0.928 mmol) and anhydrous acetone (20 mL). To this solution was added powdered sodium carbonate ($Na_2CO_3$; 98 mg, 0.928 mmol) and the mixture was stirred at room temperature for 10 min, treated with iodomethyl isobutyrate (233 mg, 1.02 mmol) dropwise via syringe, and the reaction mixture was stirred at ambient temperature under $N_2$ for 18 h. The acetone solution was filtered through a small plug of $SiO_2$ and the filtrate was concentrated to dryness by rotary evaporation. The crude yellow foam (765 mg) was dissolved in $CH_2Cl_2$ (2 mL) and purified by flash chromatography ($SiO_2$, 70% EtOAc/hexanes) to yield the title compound as a white solid (455 mg, 79.5%): structure conforms by HPLC (retention time match to authentic unlabeled standard) and diode-array UV spectrum.

Scheme 2.

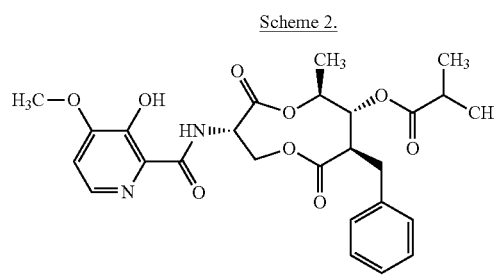

UK-²A

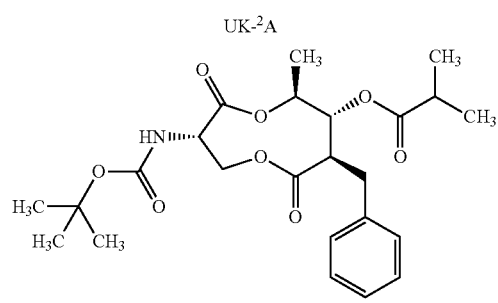

7

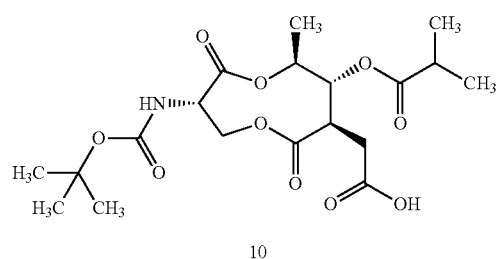

10

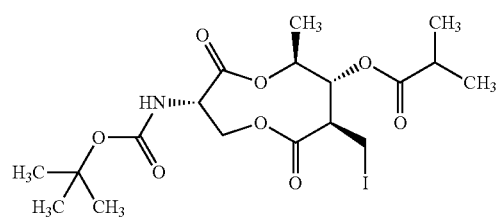

11

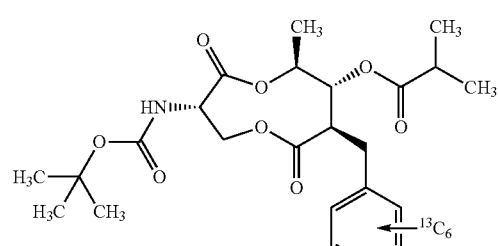

12

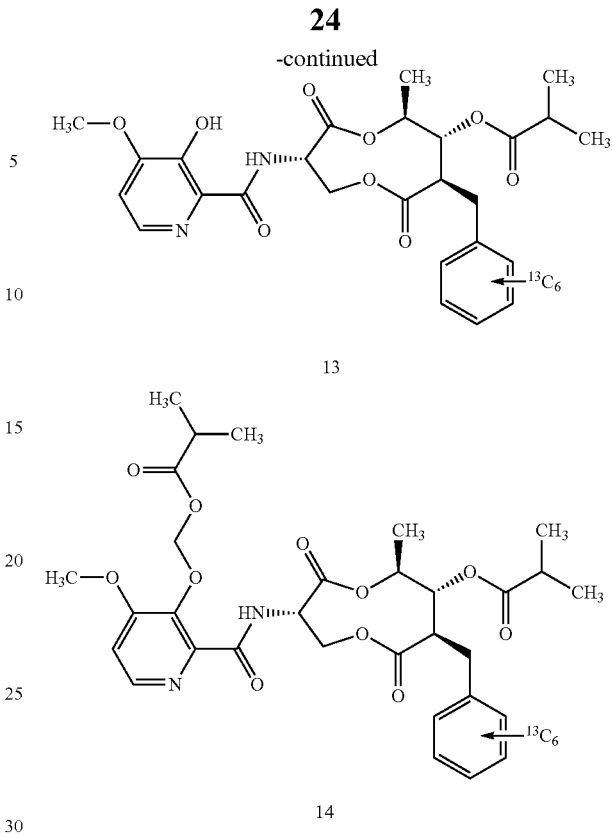

13

14

Example 2, Step 1

Preparation of (3S,6S,7R,8R)-8-benzyl-3-(tert-butoxycarbonylamino)-6-methyl-4,9-dioxo-1,5-dioxonan-7-yl isobutyrate (Compound 7)

To a suspension of (3S,6S,7R,8R)-8-benzyl-3-(3-hydroxy-4-methoxypicolinamido)-6-methyl-4,9-dioxo-1,5-dioxonan-7-yl isobutyrate (UK-2A; 10 g, 19.4 mmol) and DMAP (237 mg, 1.9 mmol) in CH$_3$CN (49 mL) was added BOC$_2$O (8.70 g, 39.8 mmol) and after a few min the reaction became homogeneous. After 30 min, N,N-diethylethylenediamine was slowly added to the homogeneous solution and stirring was continued at room temperature for 90 min. The CH$_3$CN was removed in vacuo and the resulting residue was dissolved in Et$_2$O (200 mL) and washed with 1N HCl (100 mL). The phases were separated and the aqueous phase was extracted further with Et$_2$O (25 mL), and the combined organic phases were washed with 0.5N HCl, washed with saturated aq NaHCO$_3$, dried over MgSO$_4$, filtered, and concentrated to give a white glassy solid. Purification of the crude extract by flash chromatography (SiO$_2$; 0→3% EtOAc/CH$_2$Cl$_2$) gave the title compound as a white solid (2.41 g, 27%): mp 143-145° C.; IR (neat) 1768, 1740, 1693, 1515 cm$^{-1}$; $^1$H NMR (400 MHz, CDCl$_3$) δ 7.27-7.10 (m, 5H), 5.19 (m, 2H), 5.18 (dd, J=11.9, 7.6 Hz, 1H), 4.91 (td, J=12.2, 6.0 Hz, 1H), 4.79 (s, 1H), 3.43 (s, 1H), 3.00-2.86 (m, 2H), 2.68-2.58 (m, 2H), 1.43 (s, 9H), 1.30 (d, J=6.3 Hz, 3H), 1.23 (d, J=7.0, Hz, 3H), 1.23 (d, J=7.0, Hz, 3H); $^{13}$C NMR (400 MHz, CDCl$_3$): 175.6, 171.7, 170.8, 154.7, 137.9, 128.7, 128.5, 126.6, 80.5, 75.0, 74.4, 65.9, 51.9, 51.4, 34.5, 34.1, 28.2, 18.9, 17.8 ppm; ESIMS m/z 462.5 ([M–H]$^-$).

Example 2, Step 2

Preparation of 2-((3S,7R,8R,9S)-3-(tert-butoxycarbonylamino)-8-(isobutyryloxy)-9-methyl-2,6-dioxo-1,5-dioxonan-7-yl)acetic acid (Compound 10)

To a solution of (3S,6S,7R,8R)-8-benzyl-3-(tert-butoxycarbonylamino)-6-methyl-4,9-dioxo-1,5-dioxonan-7-yl isobutyrate (10 g, 21.57 mmol) in $CH_3CN$ (72 mL), EtOAc (72 mL), and water (575 mL) were added $NaIO_4$ (134 g, 626 mmol) and ruthenium trichloride trihydrate ($RuCl_3 \cdot 3H_2O$; 282 mg, 1.08 mmol). The reaction was stirred at room temperature overnight. The resulting white suspension was diluted with water (700 mL) and extracted with $CH_2Cl_2$ (5×) and ethyl acetate (2×). Activated carbon (12 g) was added to the combined organic extracts (around 2 L) and the mixture was stirred vigorously for 1 h. The mixture was filtered through Celite®, dried over $MgSO_4$, filtered, and concentrated to give the title compound as a gray solid (7.71 g, 83%): mp 164-167° C.; IR (neat) 3375, 3293 (br), 1773, 1743, 1731, 1686, 1157 $cm^{-1}$; $^1H$ NMR (300 MHz, $CDCl_3$) δ 5.30 (m, 2H), 5.04 (t, J=9.7 Hz, 1H), 4.90 (m, 2H), 3.65 (s, 1H), 2.97 (m, 2H), 2.62 (m, 1H), 2.41 (m, 1H), 1.45 (s, 9H), 1.29 (d, J=6.2 Hz, 3H), 1.22 (d, J=7.0 Hz, 6H); $^{13}C$ NMR (101 MHz, $CDCl_3$) δ 175.78, 175.61, 171.53, 171.03, 154.88, 80.85, 74.44, 74.05, 65.56, 51.16, 45.40, 34.03, 33.44, 28.24, 18.94, 18.83, 17.77; ESIMS m/z 430.4 ([M−H]−).

Example 2, Step 3

Preparation of (3S,6S,7R,8R)-3-(tert-butoxycarbonylamino)-8-(iodomethyl)-6-methyl-4,9-dioxo-1,5-dioxonan-7-yl isobutyrate (Compound 11)

N-Methylmorpholine (2.5 mL, 23 mmol) and isobutylchloroformate (3.0 mL, 23 mmol) were added sequentially to a 0° C. solution of 2-((3S,7R,8R,9S)-3-(tert-butoxycarbonylamino)-8-(isobutyryloxy)-9-methyl-2,6-dioxo-1,5-dioxonan-7-yl)acetic acid (9.90 g, 23 mmol) in tetrahydrofuran (THF; 100 mL) in a round bottom flask wrapped with aluminum foil. After 10 min, a solution of 2-mercaptopyridine N-oxide (3.5 g, 27.5 mmol) and triethylamine (TEA; 3.8 mL, 27.5 mmol) in THF (50 mL) was added slowly and the reaction stirred at 0° C. for 1.5 h. The precipitated N-methylmorpholine hydrochloride salt was removed by filtration through a Büchner funnel with filter paper and the filtrate was concentrated in vacuo at room temperature. The oily residue was dissolved in $CH_2Cl_2$ (250 mL), iodoform (11.8 g, 30 mmol) was added, and the solution was placed in a UV reactor and irradiated with a 450 W Hg lamp with water cooling. After 1 h, the orange solution was removed from the reactor, treated with Celite®, and the solvent was removed in vacuo. The adsorbed residue was partially purified by flash chromatography ($SiO_2$, 20% EtOAc/$CH_2Cl_2$) to give a light yellow solid. Further purification by flash chromatography ($SiO_2$, 10% EtOAc/$CH_2Cl_2$) gave a dark orange solid, which was recrystallized from EtOAc/hexane to yield the title compound as an off-white solid (5.99 g, 51%): mp 168-171° C.; IR (neat) 3386, 2977, 1771, 1760, 1742, 1689, 1510 $cm^{-1}$; $^1H$ NMR (400 MHz, $CDCl_3$) δ 5.36 (s, 1H), 5.21 (m, 1H), 5.00 (t, J=9.7 Hz, 1H), 4.86 (m, 2H), 3.68 (brs, 1H), 3.31 (dd, J=11.5, 9.3 Hz, 1H), 3.02 (m, 2H), 2.63 (m, 1H), 1.45 (s, 9H), 1.27 (d, J=6.3 Hz, 3H), 1.22 (d, J=7.0 Hz, 6H); ESIMS m/z 536.3 ([M+Na]+).

Example 2, Step 4

Preparation of (3S,6S,7R,8R)-3-[(tert-butoxycarbonyl)amino]-6-methyl-4,9-dioxo-8-[($^{13}C_6$)phenylmethyl]-1,5-dioxonan-7-yl 2-methylpropanoate (Compound 12)

A 7 mL vial equipped with magnetic stir bar and rubber septum (oven dried) was charged with zinc dust (471 mg, 7.2 mmol, ground with a mortar and pestle prior to use) and anhydrous N,N-dimethylformamide (DMF; 0.70 mL). The mixture was treated with iodine ($I_2$, 183 mg, 0.72 mmol) while stirring at room temperature under $N_2$ (exothermic). After stirring for 3 min, the vial was placed in an oil bath that had been pre-heated to 40° C. and the reaction mixture was treated dropwise with a solution of (3S,6S,7R,8R)-3-((tert-butoxycarbonyl)amino)-8-(iodomethyl)-6-methyl-4,9-dioxo-1,5-dioxonan-7-yl isobutyrate (616 mg, 1.2 mmol) in warm DMF (1.20 mL). The reaction mixture was treated with a solution of ($^{13}C_6$)iodobenzene (($^{13}C_6$)PhI; 300 mg, 1.43 mmol,) in DMF (0.3 mL) followed by dichlorobis(tri-O-tolylphosphine)palladium (II) ($PdCl_2[P(o\text{-}Tol)_3]_2$; 94 mg, 0.12 mmol). The vial was purged with $N_2$, the rubber septum was replaced with a Teflon® screw cap, and the reaction mixture was heated at 40-50° C. for 30 min and then at 50-60° C. for 60 min. At this point, 90 minutes post ($^{13}C_6$)PhI addition, LC-MS showed only a minor amount of the reduced material and a major product with desired mass (around 71%). After stirring for an additional 60 min at 50-60° C., the reaction mixture was cooled to room temperature, filtered through a plug of Celite®, and the plug was washed with EtOAc (around 30 mL). The filtrate was washed with $H_2O$ (3×10 mL), washed with brine (1×10 mL), and the organic phase was dried over sodium sulfate ($Na_2SO_4$), filtered, and concentrated in vacuo to give a light yellow solid (0.59 g). The crude material was purified by flash chromatography ($SiO_2$, 0→50% EtOAc/hexanes) to give the title compound as a faint-yellow solid (0.377 g, 68%): $^1H$ NMR (400 MHz, $CDCl_3$) δ 7.49-7.27 (m, 2H), 6.99 (m, 3H), 5.28-5.11 (m, 3H), 4.97-4.72 (m, 2H), 3.43 (s, 1H), 3.02-2.83 (m, 2H), 2.74-2.56 (m, 2H), 1.43 (s, 9H), 1.30 (d, J=6.3 Hz, 3H), 1.24 (d, J=2.1 Hz, 3H), 1.22 (d, J=2.2 Hz, 3H); HRMS-ESI (m/z) [M+H]+ calcd for $C_{18}{}^{13}C_6H_{33}NO_8$: 469.2407. found, 469.2428.

Example 2, Step 5

Preparation of (3S,6S,7R,8R)-3-{[(3-hydroxy-4-methoxypyridin-2-yl)carbonyl]amino}-6-methyl-4,9-dioxo-8-[($^{13}C_6$)phenylmethyl]-1,5-dioxonan-7-yl 2-methylpropanoate (UK-2A-($^{13}C_6$)Ph, Compound 13)

A solution of (3S,6S,7R,8R)-8-($^{13}C_6$)phenylmethyl)-3-((tert-butoxycarbonyl)amino)-6-methyl-4,9-dioxo-1,5-dioxonan-7-yl isobutyrate (0.364 g, 0.775 mmol) in 1,4-dioxane (3 mL) was treated with 4M HCl in 1,4-dioxane (3 mL, 12 mmol). The flask was "sealed" with a cap and Parafilm® and stirred at room temperature for 20 h. The reaction mixture was concentrated in vacuo and the residue was triturated with $CH_2Cl_2$ and concentrated (5×10 mL). The resultant white solid was treated with $CH_2Cl_2$ (10 mL), 3-hydroxy-4-methoxypyridine-2-carboxylic acid (0.170 g, 1.008 mmol), HATU (0.442 g, 1.163 mmol), N-methylmorpholine (0.51 mL, 4.65 mmol) and a catalytic amount of DMAP. The slurry gradually turned into a clear, yellow solution. After 5 h, the reaction mixture was concentrated to one half the original volume under a stream of $N_2$, and the remaining solution was purified by flash chromatography ($SiO_2$, 0→100% EtOAc/hexanes) to give the title compound as a white solid (0.295 g, 74%): $^1$H NMR (400 MHz, $CDCl_3$) δ 11.78 (s, 1H), 8.59 (d, J=8.1 Hz, 1H), 7.99 (d, J=5.2 Hz, 1H), 7.58-7.27 (m, 2H), 7.17-6.91 (m, 3H), 6.87 (d, J=5.2 Hz, 1H), 5.35 (s, 1H), 5.26-5.12 (m, 2H), 5.06-4.91 (m, 1H), 3.94 (s, 3H), 3.62 (s, 1H), 3.06-2.88 (m, 2H), 2.78-2.68 (m, 1H), 2.62 (dt, J=14.0, 7.0 Hz, 1H), 1.33 (d, J=6.3 Hz, 3H), 1.25 (d, J=2.3 Hz, 3H), 1.23 (d, J=2.3 Hz, 3H); HRMS-ESI (m/z) [M+H]$^+$ calcd for $C_{20}{}^{13}C_6H_{30}N_2O_9$: 520.2153. found, 520.2167.

Example 2, Step 6

Preparation of {[4-methoxy-2-({(3S,7R,8R,9S)-9-methyl-8-[(2-methylpropanoyl)oxy]-2,6-dioxo-7-[($^{13}C_6$)phenylmethyl]-1,5-dioxonan-3-yl}carbamoyl)pyridin-3-yl]oxy}methyl 2-methylpropanoate (Compound 14)

A solution of (3S,6S,7R,8R)-3-{[(3-hydroxy-4-methoxypyridin-2-yl)carbonyl]amino}-6-methyl-4,9-dioxo-8-[($^{13}C_6$)phenylmethyl]-1,5-dioxonan-7-yl2-methylpropanoate (273 mg, 0.531 mmol) in anhydrous acetone (4 mL) was treated with powdered potassium carbonate (325 mesh $K_2CO_3$, 147 mg, 1.06 mmol). The slurry was treated with a solution of iodomethyl isobutyrate (145 mg, 0.637 mmol) in acetone (2 mL) while stirring at room temperature under $N_2$. After stirring for 5 h, the reaction mixture was filtered through a plug of Celite® and the plug was washed with EtOAc (30 mL). The filtrate was washed with $H_2O$ (2×10 mL), washed with brine (1×10 mL), and the organic phase was dried over $Na_2SO_4$, filtered and concentrated in vacuo to give 0.445 g of a light yellow oil. The oil was purified by flash chromatography ($SiO_2$, 0→100% EtOAc/hexanes) to give the title compound as an off-white solid (0.229 g, 70%): $^1$H NMR (400 MHz, $CDCl_3$) δ 8.53 (d, J=7.9 Hz, 1H), 8.26 (d, J=5.4 Hz, 1H), 7.50-7.28 (m, 2H), 7.13-6.97 (m, 3H), 6.95 (d, J=5.4 Hz, 1H), 5.79-5.71 (m, 2H), 5.36 (s, 1H), 5.26-5.13 (m, 2H), 5.05-4.92 (m, 1H), 3.89 (s, 3H), 3.59 (s, 1H), 3.06-2.88 (m, 2H), 2.71 (s, 1H), 2.66-2.58 (m, 1H), 2.53 (dt, J=14.0, 7.0 Hz, 1H), 1.31 (d, J=6.3 Hz, 3H), 1.25 (d, J=2.2 Hz, 3H), 1.23 (d, J=2.2 Hz, 3H), 1.13 (d, J=7.0 Hz, 6H); HRMS-ESI (m/z) [M+H]$^+$ calcd for $C_{25}{}^{13}C_6H_{38}N_2O_{11}$: 620.2677. found, 620.2681.

Scheme 3.

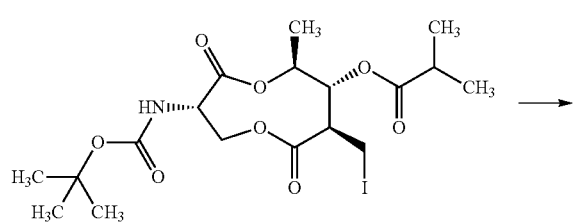

Example 3, Step 1

Preparation of (3S,6S,7R,8R)-3-[(tert-butoxycarbonyl)amino]-6-methyl-4,9-dioxo-8-[phenyl(UL-$^{14}$C)methyl]-1,5-dioxonan-7-yl 2-methylpropanoate (Compound 15)

A 7 mL vial equipped with magnetic stir bar and rubber septum (oven dried) was charged with zinc dust (605 mg, 9.25 mmol, ground with a mortar and pestle prior to use) and anhydrous DMF (0.80 mL). The mixture was treated with $I_2$ (235 mg, 0.92 mmol) while stirring at room temperature under $N_2$ (exothermic). After stirring for 3 min, the vial was placed in an oil bath that had been pre-heated to 40° C. and the reaction mixture was treated dropwise with a solution of (3S,6S,7R,8R)-3-((tert-butoxycarbonyl)amino)-8-(iodomethyl)-6-methyl-4,9-dioxo-1,5-dioxonan-7-yl isobutyrate (791 mg, 1.54 mmol) in warm DMF (1.50 mL). After stirring at 40° C. for 20 min, the reaction mixture was treated with a solution of (UL-$^{14}$C)iodobenzene (50.000 millicuries (mCi), 1.85 mmol) in DMF (0.4 mL) followed by $PdCl_2[P(o-Tol)_3]_2$ (121 mg, 0.154 mmol). The vial was purged with $N_2$, the rubber septum was replaced with a Teflon® screw cap, and the reaction mixture was heated at 40-50° C. for 30 min and then at 50-60° C. for 120 min. The reaction mixture was cooled to room temperature and filtered through a plug of Celite®, and the plug was washed with EtOAc (30 mL). The filtrate was washed with $H_2O$ (3×10 mL), washed with brine (1×10 mL), and the organic phase was dried by passing through a plug of $Na_2SO_4/MgSO_4$ in a 10 mL disposable pipet. The filtrate was concentrated in vacuo to give a light-yellow solid (0.778 g). The solid was purified by flash chromatography ($SiO_2$, 0→50% EtOAc/hexanes) to give the desired product as a peach colored solid (0.620 g, 87%): FTMS(ESI+) 464 (M+H), 416, 408, 364. HPLC analysis of the solid showed 95% chemical (UV at 254 nm) and approximately 90% radiochemical purity (β-RAM). The retention time matched an unlabeled standard of this material.

Example 3, Step 2

Preparation of (3S,6S,7R,8R)-3-{[(3-hydroxy-4-methoxypyridin-2-yl)carbonyl]amino}-6-methyl-4,9-dioxo-8-[phenyl(UL-$^{14}$C)methyl]-1,5-dioxonan-7-yl2-methylpropanoate (UK-2A-(UL-$^{14}$C)Ph, Compound 16)

The (3S,6S,7R,8R)-8-((UL-$^{14}$C)phenylmethyl)-3-((tert-butoxycarbonyl)amino)-6-methyl-4,9-dioxo-1,5-dioxonan-7-yl isobutyrate (0.620 g, 1.34 mmol) was dissolved in 1,4-dioxane (5 mL) and transferred to a 50 mL round bottom flask equipped with a magnetic stir bar. The resultant solution was treated with 4M HCl in 1,4-dioxane (5 mL, 20 mmol) while stirring at room temperature under $N_2$. After stirring for 20 h at room temperature, the reaction mixture was concentrated in vacuo. The residue was triturated with $CH_2Cl_2$ and concentrated (5×10 mL). The resultant white solid was suspended in $CH_2Cl_2$ (10 mL), and treated with 4-methoxy-3-hydroxypicolinic acid (0.294 g, 1.74 mmol), HATU (0.763 g, 2.01 mmol, 1.5 equiv,), N-methylmorpholine (0.88 mL, 8.03 mmol, 15 equiv.) and a catalytic amount of DMAP. The slurry gradually turned into a clear, yellow solution. After stirring for 22 h at room temperature, the reaction mixture was concentrated to about one half the original volume under a stream of $N_2$. The remaining solution was partially purified by flash chromatography ($SiO_2$, 0→100% EtOAc/hexanes) to give 0.453 g of a white solid. HPLC analysis indicates that this is contaminated with 15% of an non-radioactive impurity. This solid was again subjected to the flash chromatography conditions to give the title compound as a white solid (0.336 g, 49%): FTMS(ESI+) 515 (M+H). HPLC analysis of the solid showed >98% chemical (UV at 254 nm) and radiochemical purity (β-RAM). The HPLC retention time and UV spectrum matched an unlabeled standard of UK-2A.

Example 3, Step 3

Preparation of {[4-methoxy-2-({(3S,7R,8R,9S)-9-methyl-8-[(2-methylpropanoyl)oxy]-2,6-dioxo-7-[phenyl(UL-$^{14}$C)methyl]-1,5-dioxonan-3-yl}carbamoyl)pyridin-3-yl]oxy}methyl 2-methylpropanoate (Compound 17)

A solution of UK-2A-(UL-$^{14}$C)Ph (294 mg, 0.571 mmol) in anhydrous acetone (8 mL) was treated with powdered $K_2CO_3$ (111 mg, 0.800 mmol, 325 mesh). The resultant mixture was treated with a solution of iodomethyl isobutyrate (156 mg, 0.686 mmol) in acetone (2 mL) while stirring at room temperature under $N_2$. After stirring for 17 h, the reaction mixture was treated with an additional 33 microliters (μL) of iodomethyl isobutyrate (0.143 mmol, 25 mol %). After an additional 4 h, HPLC analysis showed little change. The reaction mixture was filtered through a plug of Celite®/silica gel, washing with EtOAc, and the filtrate was concentrated in vacuo to give a light-yellow foam (0.497 g). The crude material was purified by flash chromatography ($SiO_2$, 0→25% EtOAc/$CH_2Cl_2$) and the purified material was treated with $Et_2O$ and concentrated in vacuo (3×3 mL). The resultant solid was dried to constant weight under high vacuum (40-50° C.) to give the desired product as a white solid (215 mg, 61%): FTMS(ESI+) 615 (M+H). The total radioactivity was found to be 10.182 mCi with a specific activity of 29.1 mCi/mmol. HPLC analysis of the solid showed >98% chemical (UV at 254 nm) and radiochemical purity (β-RAM). The HPLC retention time and UV spectrum matched an unlabeled standard of Compound 17.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

What is claimed is:

1. A radiolabeled compound of the following formula:

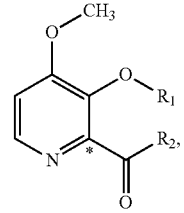

$* = {}^{14}C$

Wherein $R_1$ is selected from the group consisting of:
H and

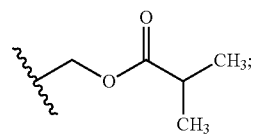

$R_2$ is selected from the group consisting of
OH and

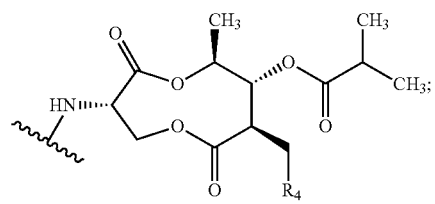

and $R_4$ is selected from the group consisting of Ph, ($^{13}C_6$)Ph, and (UL-$^{14}$C)Ph.

2. The compound according to claim 1, wherein $R_1$ is

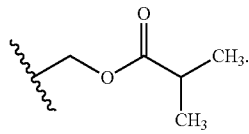

3. The compound according to claim 1, wherein $R_2$ is:

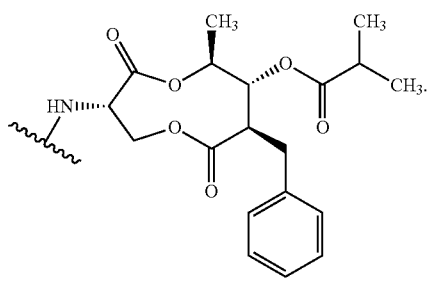 [SMILES: *N[C@H]1COC(=O)[C@H](Cc2ccccc2)[C@@H](OC(=O)C(C)C)[C@H](C)OC1=O]

4. The compound according to claim 1, wherein $R_1$ is H.

5. The compound according to claim 1, wherein the compound is:

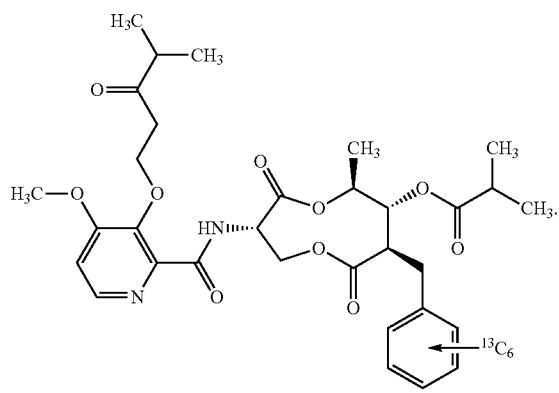

6. An isotopically labeled compound of the following formula:

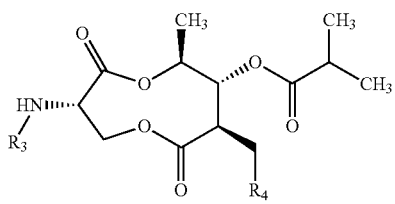

wherein $R_3$ is selected from the group consisting of:
H,

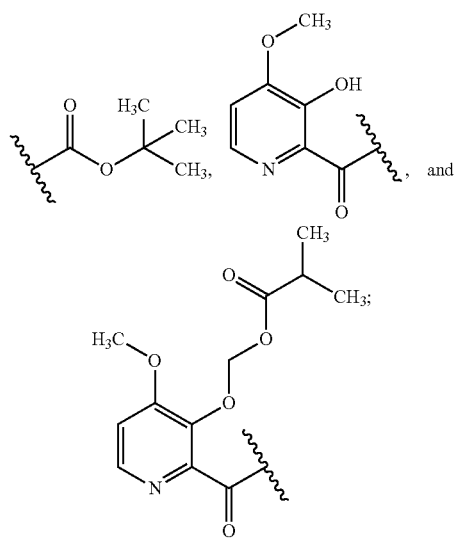

and $R_4$ is selected from the group consisting of ($^{13}C_6$)Ph and (UL-$^{14}$C)Ph.

7. The compound according to claim 6, wherein $R_3$ is:

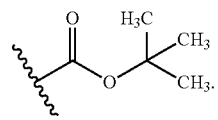

8. The compound according to claim 6, wherein $R_3$ is:

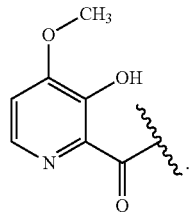 [SMILES: *C(=O)c1nccc(OC)c1O]

9. The compound according to claim 6, wherein $R_3$ is:

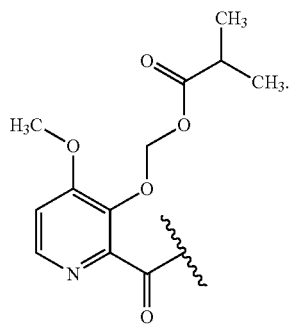 [SMILES: *C(=O)c1nccc(OC)c1OCOC(=O)C(C)C]

10. The compound according to claim 6, wherein $R_4$ is ($^{13}C_6$)Ph.

11. The compound according to claim 6, wherein $R_4$ is $(UL-^{14}C)Ph$.

12. A method for studying the biosphere, comprising the steps of:

exposing samples to an isotopically labeled compound selected from the group consisting of (a) and (b), wherein:

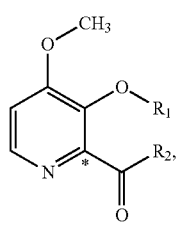 (a)

$* = ^{14}C$ wherein $R_1$ is selected from the group consisting of H and

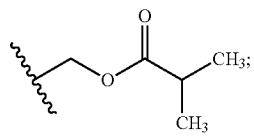

$R_2$ is selected from the group consisting of OH and

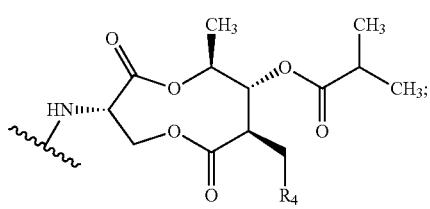

and $R_4$ is selected from the group consisting of Ph, $(^{13}C_6)Ph$, and $(UL-^{14}C)Ph$; and

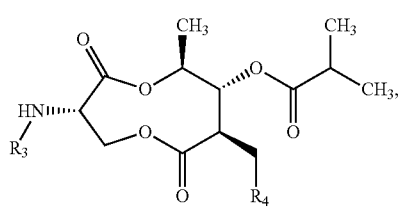 (b)

wherein $R_3$ is selected from the group consisting of:

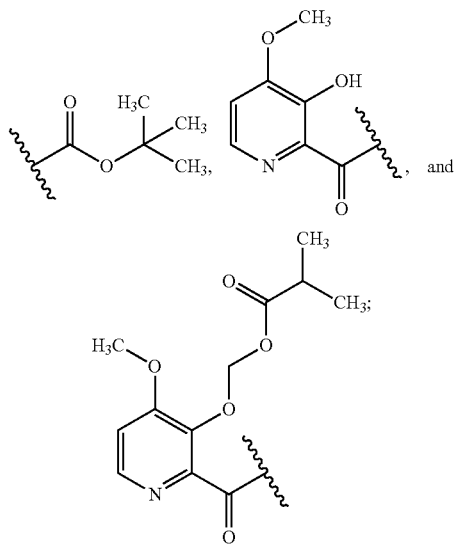

and $R_4$ is at least one atom selected from the group consisting of Ph-$^{13}C_6$ and Ph-UL-$^{14}C$; and determining which samples include an isotopically labeled signature from said compound.

13. The method according to claim 12, wherein the compound is (a) and the sample is a portion of a plant.

14. The method according to claim 12, wherein the compound is (a) and the sample is from a surface adjacent to a plant.

15. The method according to claim 12, wherein the compound is (a) and the sample is from a material that is in communication with a surface adjacent to a plant.

16. The method according to claim 12, where the compound is (a).

17. The method according to claim 12, wherein the compound is (b) and the sample is a portion of a plant.

18. The method according to claim 12, wherein the compound is (b) and the sample is from a surface adjacent to a plant.

19. The method according to claim 12, wherein the compound is (b) and the sample is from a material that is in communication with a surface adjacent to a plant.

20. The method according to claim 12, where the compound is (b).

* * * * *